United States Patent
Brill et al.

(10) Patent No.: US 10,295,329 B2
(45) Date of Patent: May 21, 2019

(54) MONITORING SYSTEM AND METHOD FOR VERIFYING MEASUREMENTS IN PATTERNED STRUCTURES

(75) Inventors: Boaz Brill, Rehovot (IL); Boris Sherman, Rehovot (IL); Igor Turovets, Moshav Givat Yarim (IL)

(73) Assignee: NOVA MEASURING INSTRUMENTS LTD., Rehovot (IL)

( * ) Notice: Subject to any disclaimer, the term of this patent is extended or adjusted under 35 U.S.C. 154(b) by 627 days.

(21) Appl. No.: 14/236,199

(22) PCT Filed: Aug. 1, 2012

(86) PCT No.: PCT/IL2012/050283
§ 371 (c)(1),
(2), (4) Date: Jan. 30, 2014

(87) PCT Pub. No.: WO2013/018093
PCT Pub. Date: Feb. 7, 2013

(65) Prior Publication Data
US 2014/0195194 A1  Jul. 10, 2014

Related U.S. Application Data

(60) Provisional application No. 61/513,693, filed on Aug. 1, 2011.

(51) Int. Cl.
*G03F 7/20* (2006.01)
*G01B 11/02* (2006.01)

(52) U.S. Cl.
CPC .......... *G01B 11/02* (2013.01); *G03F 7/70625* (2013.01)

(58) Field of Classification Search
None
See application file for complete search history.

(56) References Cited

U.S. PATENT DOCUMENTS 6,982,793 B1 * 1/2006 Yang ................... G03F 7/70633
356/401
7,233,870 B1 * 6/2007 Dalrymple ........... G06K 9/0051
702/76

(Continued)

OTHER PUBLICATIONS

Andrea Saltelli, "Global Sensitivity Analysis: The Primer", Jan. 2008, Wiley, p. 156.*

(Continued)

*Primary Examiner* — Alexander Satanovsky
*Assistant Examiner* — Brent A. Fairbanks
(74) *Attorney, Agent, or Firm* — Alphapatent Associates, Ltd; Daniel J. Swirsky

(57) ABSTRACT

A method and system are presented for monitoring measurement of parameters of patterned structures based on a predetermined fitting model. The method comprises: (a) providing data indicative of measurements in at least one patterned structure; and (b) applying at least one selected verification mode to said data indicative of measurements, said at least one verification mode comprising: I) analyzing the data based on at least one predetermined factor and classifying the corresponding measurement result as acceptable or unacceptable, II) analyzing the data corresponding to the unacceptable measurement results and determining whether one or more of the measurements providing said unacceptable result are to be disregarded, or whether one or more parameters of the predetermined fitting model are to be modified.

21 Claims, 12 Drawing Sheets

(56) References Cited

U.S. PATENT DOCUMENTS

| | | | |
|---|---|---|---|
| 2003/0190793 A1* | 10/2003 | Brill | G01N 21/4788 |
| | | | 438/401 |
| 2004/0203177 A1 | 10/2004 | Davis et al. | |
| 2004/0223137 A1* | 11/2004 | Littau | G03F 7/70491 |
| | | | 356/123 |
| 2009/0160027 A1* | 6/2009 | Park | G03F 1/144 |
| | | | 257/618 |
| 2011/0026032 A1* | 2/2011 | Den Boef | G01N 21/9501 |
| | | | 356/446 |

OTHER PUBLICATIONS

Sean Hannon et al: "Utilizing overlay target noise metrics for improved process control", Proceedings of SPIE, May 10, 2005, pp. 1173-1179.

Shinn-Sheng Yu et al: "OCD metrology by floating n/k", Proceedings of SPI, vol. 6518, Jan. 1, 2007, pp. 65183C-65183C-8.

* cited by examiner

MONITORING SYSTEM AND METHOD FOR VERIFYING MEASUREMENTS IN PATTERNED STRUCTURES

TECHNOLOGICAL FIELD AND BACKGROUND

Optical Critical Dimension (also termed "optical CD" or "OCD") measurement techniques (known also as Scatterometry) are known as efficient techniques for measuring parameters of patterned (periodic) structures. Measurement of these parameters provides a viable metrology solution for process control in high volume manufacturing of semiconductor devices.

OCD measurements are usually performed using a fitting procedure. According to this procedure, theoretical model describing a structure under measurements is used to generate theoretical data or reference data, and the latter is iteratively compared to measured data, while varying the model parameters until the "best fit" is found. The parameters of the "best fit" model are considered as corresponding to the measured parameters. Measured data (typically optical data) can be analyzed to derive information regarding the geometrical parameters of patterns including thicknesses, critical dimension (CD), line spacing, line width, wall depth, wall profile, etc., as well as optical constants of materials included in a sample being measured.

Optical metrology tools used for such measurements are typically ellipsometry and/or reflectometry based tools. Reflectometry based tools typically measure changes in the magnitude of radiation, whether un-polarized or polarized returned/transmitted from/through the sample, and ellipsometry based tools typically measure changes of the polarization state of radiation after interacting with the sample. In addition or as alternative to these techniques, angular analysis of light returned (reflected and/or scattered) from a patterned (periodic) structure could be used to measure the parameters that define/characterize the structure.

GENERAL DESCRIPTION

While optical CD has proven its process control benefits, it suffers from perceptual credibility drawback relative to image-based metrology techniques, which are considered more direct hence more credible. One of the reasons is that measured spectra are not readily interpreted by the human eye (as opposed to microscopy images). Hence, possible errors in data (e.g. due to the measurement tool malfunction), might be unnoticed and harm the model fitting. Another reason is that the scatterometry theoretical modeling usually contains prior assumptions, such as that some semiconductor materials are stable and known, that certain geometrical parameters can be assumed fixed, etc. Deviations of reality from these assumptions will induce some error in the fitting process and hence in the measurement results, and in most cases such error is not easily identified or quantified. The potential damage of these errors is sub-optimal control of the manufacturing process possibly creating a semiconductor yield issue.

There is thus a need in the art for a novel technique for measuring parameter(s) of a patterned structure, utilizing verification of measurements to determine as to whether disregard certain measurement, or whether modify one or more parameters of a fitting model. In this connection, it should be understood that the present invention provides verification of measurements by applying one or more verification modes to data indicative of measurements, where such data may include raw measured data (i.e. before fitting) or measurement health data; and/or measured data corresponding to a desired degree of fit with the model; and/or measurement/metrology result (i.e. structure parameter(s) calculated from the fitting procedure). At times, in the description below, all these categories of data indicative of measurements are referred to as "measured data", but this term should be interpreted correctly as defined above.

The present invention provides several key performance metrics that together constitute a verification methodology that can act as a safeguard against scatterometry errors of different types and can flag potentially erroneous measurement results. The invention is based on the understanding of the following. As indicated above, scatterometry is typically based on fitting a theoretical (simulated) model data or signal to a measured spectral (diffraction) signature from a patterned (periodic) structure. Currently, during setup (off-line), theoretical model is tested and matched to all available measurement samples, i.e. for calculation accuracy and/or geometrical description and/or materials, etc. During actual (on-line) measurements of new unknown samples with set-up model, there still can be several possible factors that could potentially cause an error in measurements. These factors may be associated with a mismatch between theoretical model and measurement sample, such as deficiency of geometrical description of stack structures (e.g. missing layer, absence of corner rounding, etc.), inaccurate model of material optical properties (e.g. material variability not taken into account), assumption of nominal fixed value for some stack parameter is not true for the sample (different constant value or variable value). Also, these factors may be associated with measurement data inaccuracies including systematic measurement errors (e.g. due to problem in at least one of calibration, pattern recognition, focus and/or other measurement tool sub-systems), level of random noise beyond the acceptance level for the particular tool.

The present invention provides for detection of scatterometry erroneous measurements (on the metrology tool). This could be achieved by introduction of a verification module including at least one error indicator (EI) utility, or combinations of multiple error indicator utilities each one designed to flag one or more potential measurement problems of different types. The output data of multiple EI's could be further combined into a single Verification Figure of Merit (VFM), e.g. termed "score", characterizing the quality of the measurement. By placing a control limit (threshold) on VFM the system could flag out any particular measurement that does not comply with required measurement quality and the scatterometry metrology tool can be used in a safer, more reliable way. The reason for flagged measurements can be further analyzed based on EI information allowing user to decide whether correction action is required or results of the measurements can be used for the purpose of process control.

Error indicators can be based on any single measurement as well as on wafer statistics. For all error indicators, confidence and score limits can be set during the recipe setup (off-line) steps. These limits are part of the measurement recipe and are used for calculation of verification figure of merit when recipe is used for production measurements.

Thus, according to one broad aspect of the invention, there is provided a method for monitoring measurement of parameters of patterned structures, said measurement of the parameters of patterned structures being based on a predetermined fitting model, the method comprising:

(a) providing data indicative of measurements in at least one patterned structure, to enable determination of at least one parameter of the patterned structure;

(b) applying at least one selected verification mode to said data indicative of measurements said at least one verification mode comprising: analyzing the data based on at least one predetermined factor and classifying corresponding measurement result as acceptable or unacceptable, thereby enabling to determine whether one or more of the measurements providing said unacceptable result are to be disregarded, or whether one or more parameters of the predetermined fitting model are to be modified.

As indicated above, the data indicative of measurements includes at least one of the following types of data: raw measured data, measurement health data, data corresponding to a desired degree of fit with the fitting model, and measurement result in the form of one or structure parameters calculated from a fitting procedure.

The desired degree of fit is typically defined by a merit function or goodness of fit factor. In some embodiments, the application of the selected verification mode may comprise analyzing multiple values of the merit function determined for multiple measurement sites respectively, and upon determining that said multiple values of the merit function include at least one value that differs from other of said multiple values by a value exceeding certain threshold, classifying the corresponding measurement as unacceptable result. The multiple measurement sites may comprise at least one control site having a configuration corresponding to at least one other measurement site and being characterized by a smaller number of floating parameters of the structure. In some embodiments, application of the selected verification mode comprises analyzing at least two merit functions determined for a control site and at least one measurement site respectively, and upon determining that a difference between the merit functions of the control site and said at least measurement site differs by a value exceeding certain threshold, classifying the corresponding measurement as the unacceptable result. In some embodiments, the merit function is utilized for determining a measurement result in the form of at least one parameter of the patterned structure, for each of a control site and at least one measurement site.

In some embodiments, the raw measured data comprises at least two data pieces corresponding to at least two different measurement conditions respectively. At least one model based measured parameter corresponding to a predetermined degree of fit with the raw measured data piece may be utilized for each of said at least two data pieces, and the at least one parameter of the patterned structure is determined. In this case, the application of the selected verification mode may comprise analyzing at least two values of said at least one parameter of the patterned structure corresponding to said at least two different measurement conditions, and upon determining that a difference between said at least two values exceeds a certain threshold, classifying the corresponding measurement as unacceptable result. The data indicative of measurements may comprise spectral data, in which case the at least two data pieces may correspond to at least two different sets of wavelengths respectively. In some other examples, the at least two data pieces correspond to at least two different angles of incidence of radiation onto the structure, and/or angles of radiation propagation from the structure, utilized in the measurements; as well as at least two data pieces correspond to at least two different polarizations of radiation utilized in the measurements.

In some embodiments, the raw measured data is in the form a multi-point function of a measured response of the structure to incident radiation. The application of the selected verification mode may comprise comparing the multi-point function of a measured response with a theoretical model-based function corresponding to a predetermined degree of fit with the measured response, to enable to determine whether said multi-point function includes at least one function value for at least one measurement point that differs from the function values at other measurement points by a value exceeding certain threshold.

In some embodiments, the application of the selected verification mode comprises determining a number of iteration steps applied to reach the desired goodness of fit condition, and upon identifying that said number exceeds a certain threshold, classifying the corresponding measurement as the unacceptable result.

In some embodiments, said raw measured data may correspond to the measurements performed on the same measurement site and comprising measured signals successively obtained from said measurement site, and may further comprise an integrated measured signal formed by said serious of measured signals successively measured on the same measurement site. The application of the selected verification mode may comprise comparing the measured signals with one another to determine whether there exists at least one measured signal that differs from other measured signals by a value exceeding certain threshold; and/or comparing the measured signals with the integrated measured signal to determine whether there exists at least one measured signal that differs from the integrated measured signal by a value exceeding certain threshold.

According to another broad aspect of the invention, there is provided a monitoring system for controlling measurements of parameters of patterned structures, the system comprising:

(a) data input utility for receiving data indicative of measurements in at least one patterned structure;

(b) a memory utility for storing at least one fitting model; and (c) a processor utility comprising:
   a fitting utility configured and operable for utilizing said at least one fitting model to determine a measurement result in the form of at least one parameter of the patterned structure;
   a verification module comprising one or more error indicator utilities each configured and operable for applying at least one verification mode to data indicative of measurements, said at least one verification mode comprising: analyzing said data based on at least one predetermined factor and classifying corresponding measurement as acceptable or unacceptable and generating output data indicative thereof, thereby enabling to determine whether one or more of the unacceptable measurements are to be disregarded, or whether one or more parameters of the predetermined fitting model are to be modified.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figure 1:
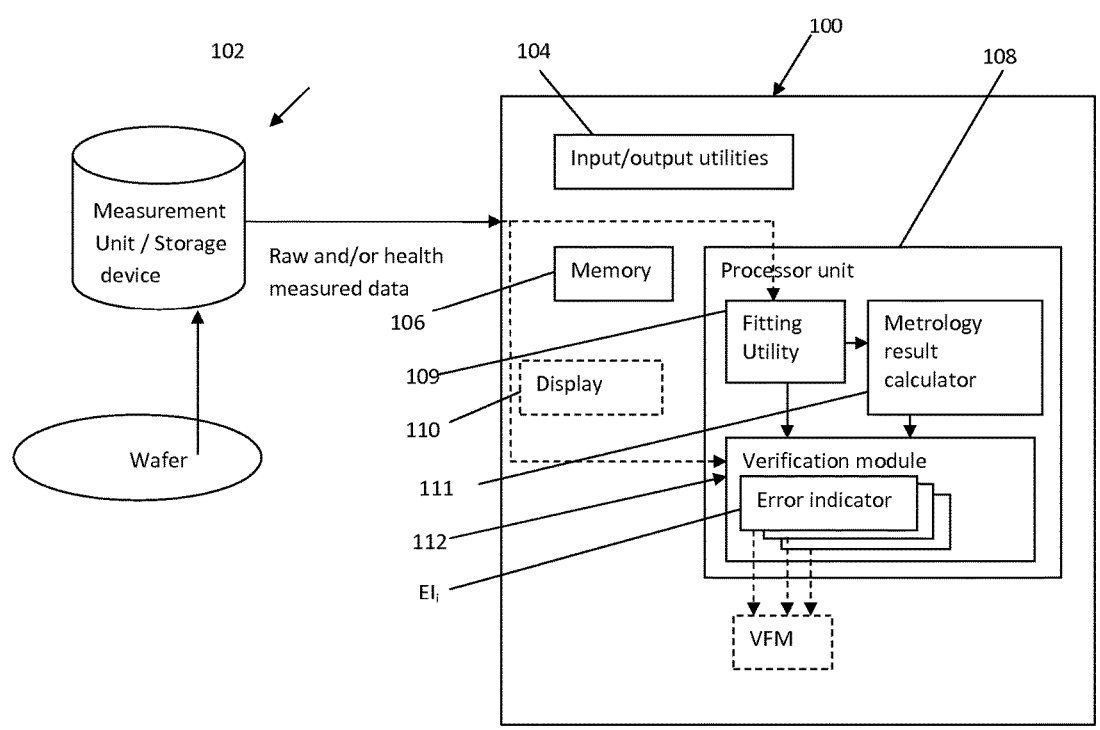
FIG. 1 is a block diagram of a monitoring system of the present invention for controlling optical measurements in patterned structures.

Referring to FIG. 1, there is schematically illustrated, by way of a block diagram, a monitoring system 100 configured and operable for controlling measurements of parameters of patterned structures. The system 100 operates as a data verification system, which is connectable (via wires or wireless signal transmission) to a measurement unit 102. The data verification system 100 is a computer system including inter alia such functional utilities as data input/output utilities 104, memory utility 106, data processor unit 108, and possibly a display 110. The processor unit 108 includes a fitting utility 109, a structure (wafer) parameter (metrology result) calculator 111, and a verification module 112 which includes one or more error indicator utilities, generally at $EI_i$. Each error indicator utility is configured and operable to perform one or more verification modes with respect to data indicative of measurements. As indicated above, data to be verified includes one or more of the following: raw measured data (before fitting), health measured data, —measured data described by a degree of fit with the model (goodness of fit (GOF), merit function (MF), measurement/metrology result (i.e. structure parameter(s) calculated from the fitting procedure. The error indicator utility operates to process/analyze the data indicative measurements (provided off-line or on-line), and generate output data (flag) indicative of one or more potential measurement problems. In a specific but not limiting example, each error indicator utility is configured for determining/flagging a problem of a different type. As further shown in the figure, output data from multiple error indicators may be combined into a single Verification Figure of Merit utility (VFM) 114 that characterizes the quality of the measurement.

Figure 2:
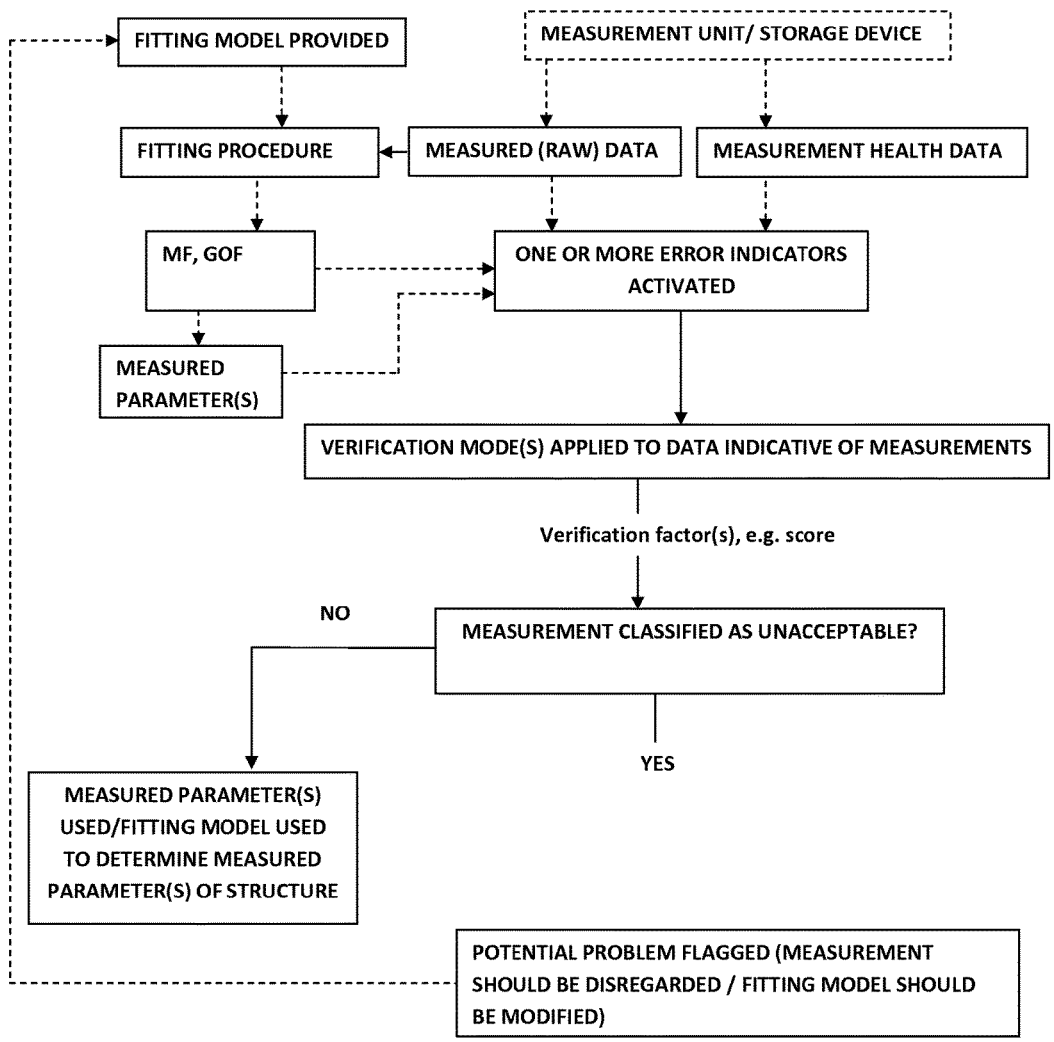
FIG. 2 is a flow chart exemplifying a method of the invention for controlling optical measurements in patterned structures.

Reference is made to FIG. 2 exemplifying a flow chart 200 of a method of the invention carried out by the monitoring system 100. Initially, one or more fitting models are selected and stored in the memory utility 106 (as a part of recipe design, e.g. resulting from a learning mode). The system receives data indicative of optical measurements carried out in at least one measurement site in one or more patterned structures (e.g. multiple lots). The data indicative of measurements may be received directly from the measurement unit (on-line mode) or may be received from a data storage device which may be that of the measurement unit or not (off-line mode). The received data may be raw measured data corresponding to the measurements on at least one measurement site. This may be a series of detected optical response signals (e.g. from the same measurement site), or a multi-point function of a measured response of the structure to incident radiation, or a spectral signature. Alternatively or additionally, the received data may include health measured data, fitting data, metrology result. The processor unit 108 operates to activate one or more of the error indicators $EI_i$ of the verification module to apply at least one selected verification mode to the received data to verify said data and generate output data indicative thereof. The verification mode includes analyzing the received data using one or more verification factors (threshold based factors), and classifying the corresponding measurement(s) as acceptable or unacceptable. Optionally, data corresponding to the unacceptable measurement/result can be further analyzed to determine whether one or more measurements providing the unacceptable result are to be disregarded, or whether one or more parameters of a fitting model are to be modified.

The following are some examples of the configuration and operation of the verification module 112. It should be noted that the present invention is exemplified herein as relating to scatterometry measurements, where measured data may be in the form of spectral signature. However, the principles of the invention are not limited to this specific application, and the invention can generally be used with any model-based measurement technique, namely a technique where measured data is interpreted by model (fitting procedure) and the sample's parameters of interest are derived from the model values corresponding to the best fit with the measured data. Also, the invention is exemplified herein as relating to measurements taken on semiconductor wafers. However, it should be understood that the invention is not limited to this specific application, and sample/structure under measurements may be any patterned structure. The parameters to be measured may include features of the pattern (e.g. critical dimensions), as well as layers' thicknesses.

Figure 3:
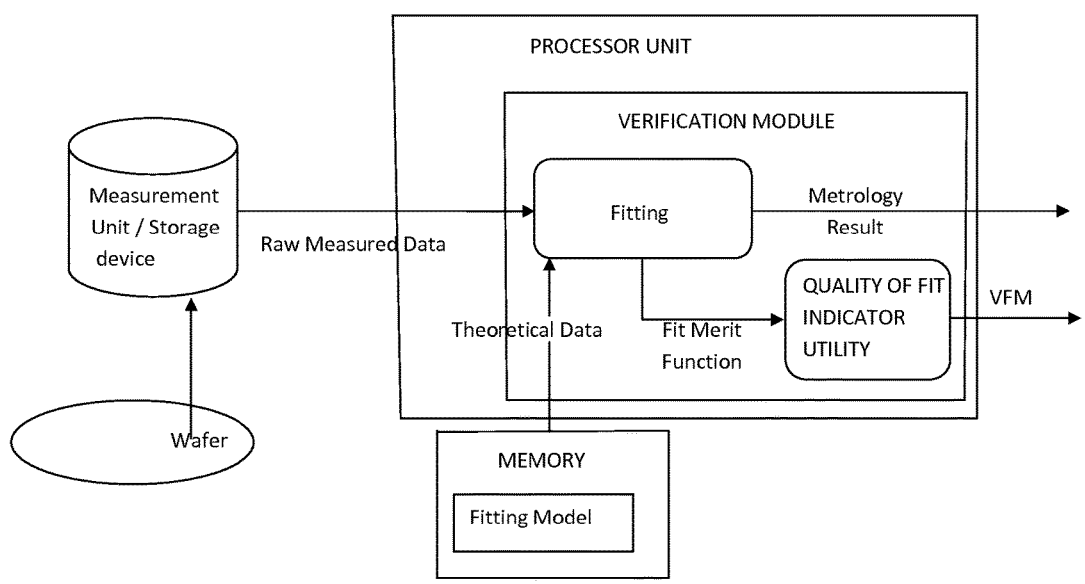
FIG. 3 exemplifies operation of the monitoring system of FIG. 1 in which the error indicator module includes a so-called quality of fit indicator utility.

Reference is made to FIG. 3 exemplifying the operation of the monitoring system 100 in which the verification module 112 includes a so-called quality of fit indicator utility. The processor unit receives data indicative of measurements in the form of raw measured data corresponding to the measurements on multiple measurement sites, and activates the quality of fit indicator utility. The latter applies a selected fitting model (from the memory utility) to the raw data (i.e. performs fitting procedure), determines a merit function (constituting a model based measured parameter corresponding to at least one parameter of the patterned structure) for each of the measurement sites corresponding to a predetermined degree of fit with the raw data. Then, the error indicator utility operates to perform the selected verification mode. To this end, multiple values of the merit function for multiple measurement sites are analyzed. If there exists at least one merit function value that differs from other values by a value exceeding a predetermined threshold, the error indicator utility classifies the corresponding measurement result as unacceptable and generates corresponding output data; otherwise, the processor unit may utilize the merit functions to calculate the structure parameter(s) (metrology result).

As indicated above, fitting merit function may be computed as a function of differences between theoretical and experimental diffraction signatures. The fitting merit function is typically used as the minimization parameter in the fitting process, i.e. model parameters are repeatedly modified and the fitting merit function is re-calculated until the fitting merit function reaches a minimum. Once the best fit between model and given measurement data is achieved, the final value of the fitting merit function represents the residual mismatch error that cannot be described under the assumption of the current model. If the residual value of fitting merit function is beyond the standard level as defined at model setup, this is an indicator of possible problem, e.g. one of the model assumptions was violated in measured data.

Figure 4A:
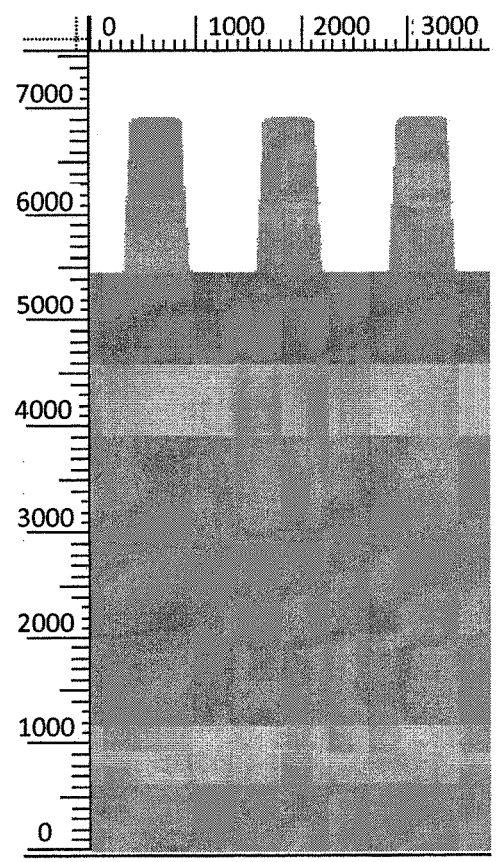
FIG. 4A shows a schematic cross section of a typical periodic structure.

In this connection, reference is made to FIGS. 4A to 4D. FIG. 4A shows a schematic cross section of a typical periodic structure (only three periods shown) on which scatterometry measurements are taken, including multiple uniform layers and a periodic line array of photoresist at the top layer. The optical properties of one of the materials in the stack have been deliberately modified in one of the measurement sites, while the theoretical model used the constant material properties.

Figure 4B:
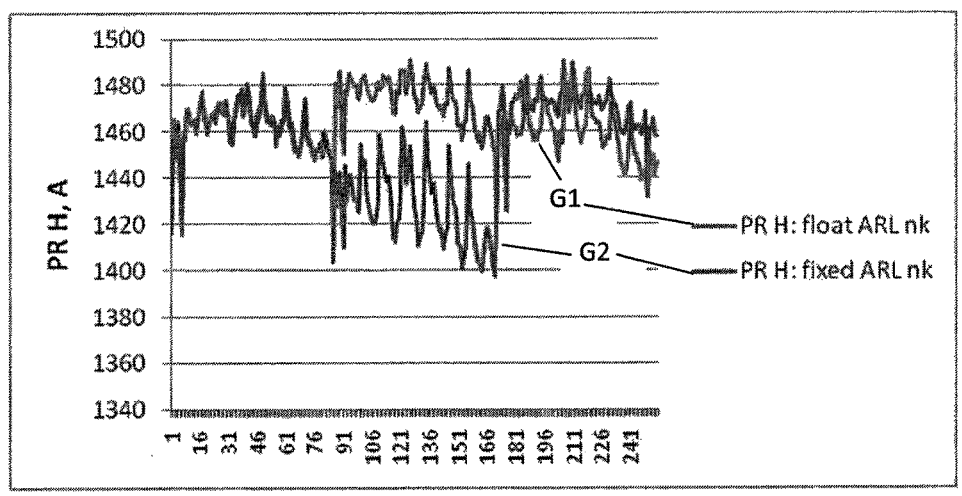
FIG. 4B shows measured values of the profile height for the structure of FIG. 4A with and without floating material properties.

FIG. 4B shows measured values of the profile height for the structure of FIG. 4A with and without floating material properties (graphs G1 and G2 respectively). Here, the measurement results are shown in graph G2, indicating that the profile height values became significantly lower in one of the measurement sites.

Figure 4C:
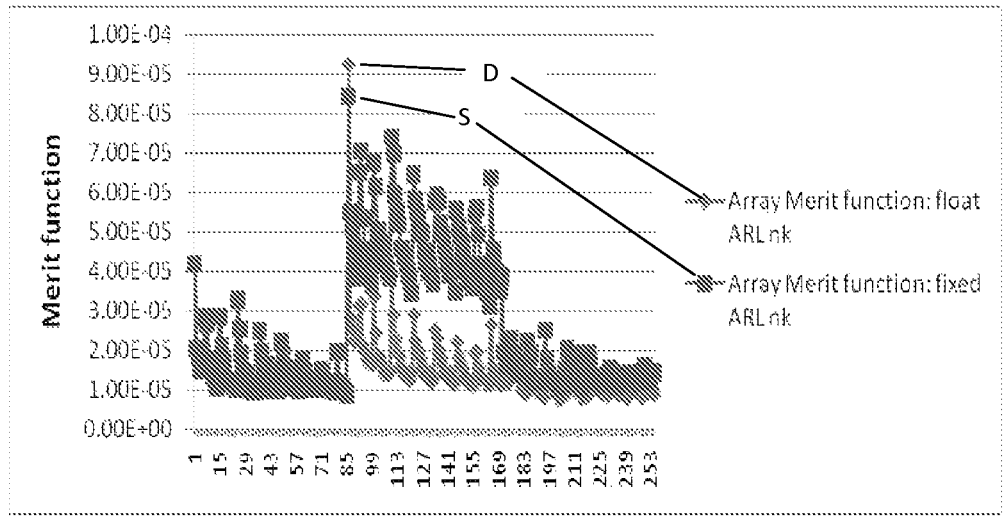
FIG. 4C illustrates the merit function results for multiple points on three measurement sites in the structure of FIG. 4A.

FIG. 4C illustrates the merit function results for multiple points on three measurement sites. The material properties of one of the layers in the structure have been deliberately modified for one measurement site, as indicated by the higher merit function values obtained while n&k (material properties) have been kept constant (squares S). When floating the n&k values, the merit function levels are recovered to the same levels of the other two sites (diamonds D). As shown in FIG. 4C, the fitting merit function clearly indicates that its values for specific measurement site are significantly higher than for other sites, thus correctly flagging the suspicious measurements. By including variable material properties into the model (G1, D), the correct measurement of the profile height and fitting merit function values can be recovered.

Figure 4D:
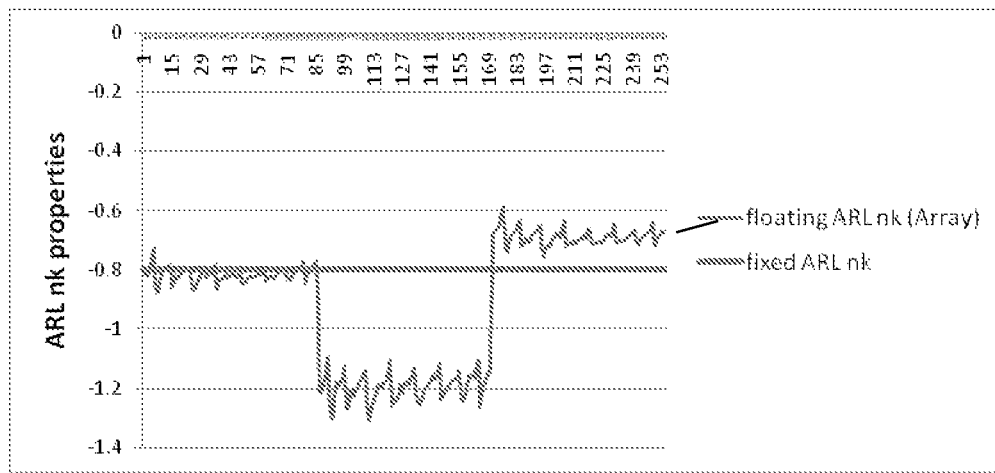
FIG. 4D shows measured values of the material properties of the changing layer in the structure of FIG. 4A, as reconstructed by the fitting procedure in the case of having floating variable.

FIG. 4D shows measured (relative) values of the material properties of the changing layer (similar to the example of FIG. 4C) as reconstructed by the fitting procedure in the case of having floating variable.

Figure 5:
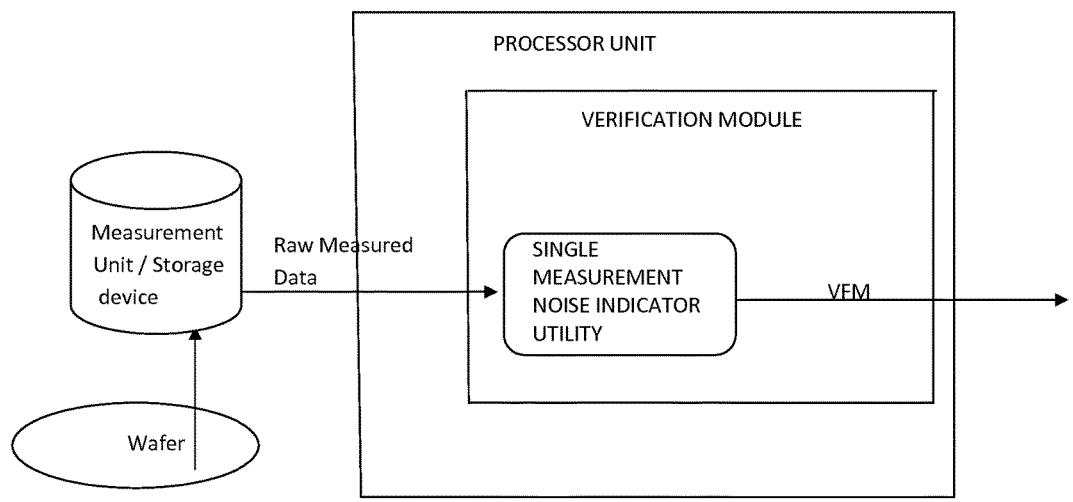
FIG. 5 exemplifies operation of the monitoring system of FIG. 1 in which the error indicator module includes a so-called single measurement noise indicator utility.

Reference is made to FIG. 5 exemplifying the operation of the monitoring system 100 in which the verification module 112 includes a so-called single measurement noise indicator utility. The data to be verified may be in the form of raw measured data corresponding to the measurements performed on the same measurement site and comprising a sequence/set of measured signals successively obtained from said measurement site, or an integrated measured signal formed by such serious of measured signals. The error indicator utility applies the verification mode to the raw measured data. The verification mode may include comparison between the measured signals with one another, to determine whether there exists at least one measured signal that differs from other measured signals by a value exceeding certain threshold. Alternatively or additionally, the verification mode may include comparison between each of the measured signals and the integrated measured signal, to determine whether the measured signals include at least one measured signal that differs from the integrated measured signal by a value exceeding certain threshold.

In this connection, the following should be understood. The repeatability of the measurement results (after fitting) is probably the most used quality metric in off-line data analysis and tool qualification. Low repeatability is an indicator for possible tool issues, e.g. high noise or stability problems, but it can also indicate a change in one of the model's assumptions. If for example a parameter that has been assumed fixed is changing, the solution becomes not only less accurate but also less stable, hence the repeatability of certain parameters will be downgraded. Repeatability testing procedure is usually performed only in dedicated tests, due to considerable time required for repeated data collection steps with production non-worthy throughput. However, there are several options to evaluate the repeatability with minimal throughput impact, if it is possible to measure the measured data noise. To evaluate the noise in real time, on the real target (site, wafer), one of the following can be used.

In some situations, the data being interpreted can be (or already is) collected in a sequence of short exposures rather than a single long exposure. Typically the different exposures are averaged out to minimize noise. However, if read separately, the short exposures can be used to evaluate the remaining noise in the averaged result. For example assuming Gaussian random noise, the RMS of the noise in the average will be the RMS of the noise in each single measurement divided by the square root of the (known) number of single measurements in the average.

Another example is based on that in many cases a statistical indicator is needed (e.g. for a wafer or a lot) rather than an indicator for a specific measurement, and accordingly repeatability can also be evaluated using a bootstrapping methods. More specifically, a second measurement may be collected on some of the sites (e.g. one per wafer), logging the difference between the two measurements and accumulating the differences along time in order to obtain a representative value for the typical noise. If for example a full lot (25 wafers) is being measured and a single site (die) is measured twice per wafer, a reliable measurement of the spectral noise can be established per lot with minimal throughput hit to the overall system.

During recipe setup the impact of spectral noise on the recipe performance is defined with sensitivity and correlation analysis and stored in the recipe, to be later used during the measurements to calculate impact of measured spectral noise on all floating parameters.

Figure 6:
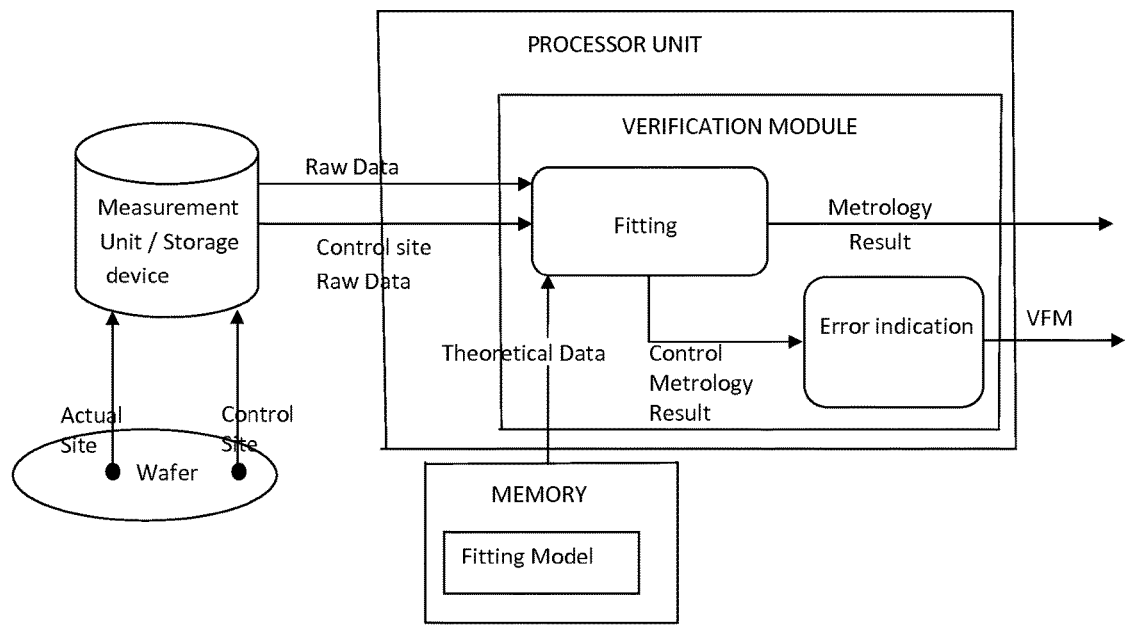
FIG. 6 exemplifies operation of the monitoring system of FIG. 1 in which the error indicator module includes a control site error indicator also termed "parallel interpretation indicator utility"

Reference is made to FIG. 6 exemplifying the operation of the monitoring system 100 in which the verification module 112 includes a control site error indicator also termed "parallel interpretation indicator utility". In this example, received data includes raw measured data indicative of optical measurements taken on multiple (generally at least two) measurements sites including at least one test/control site. Considering semiconductor wafers, the test site is typically located within a margin region of the wafer, while "actual" measurement site is located within the patterned region (dies' region) of the wafer.

In some embodiments, the control site indicator utility is configured and operable to perform the verification mode with respect to the measured data pieces of the test site and one or more actual measurement sites. It should be understood that if more than one actual measurement site is considered, these may be actual measurements sites in the same wafer or similar sites in the wafers of different lots. In some other embodiments, the control site indicator utility is configured and operable to perform the verification mode with respect to the measured data pieces of different test site located in the same wafer or similar wafers of different lots.

Thus, the processor unit receives two types/pieces of the raw measured data including measured data from either the control/test site and measured data from the "actual" measurement site located in the patterned area of the wafer, or measured data from different test sites. The processor unit operates to process the measured data pieces by applying thereto a selected fitting model (i.e. performs fitting procedures for each of the raw measured data pieces), and determining the respective merit function values (corresponding to the best fit condition).

Then, in some embodiments, the verification mode may include comparison between the merit function values for the different sites and determining whether a difference between them exceeds a predetermined threshold corresponding to unacceptable condition for the measured data of the actual measurement site. In some other embodiments, the merit function values can be used for determining the respective values of a certain parameter of the structure (metrology result), and then the selected verification mode is applied to the metrology results for the different sites, rather than to the merit function values, to determine whether a difference between these parameter values exceeds a predetermined threshold, corresponding to unacceptable measured data from the actual measurement site.

In this connection, the following should be noted. One of the reasons for errors in scatterometry might relate to the ability of the fitting model to compensate un-modeled differences due to multiple cross correlated floating parameters. As a result, one may get measurement bias that might go unnoticed due to relatively good fit. In order to overcome such difficulty, additional measurement on the control site(s) may be used to validate the quality of the measurement. Such control sites could be simpler sites which do not require as many floating parameters, for example non-patterned ("solid") sites in which all layers are uniform within the area of the measurement spot in the test site. The lower number of floating parameters can allow such sites to be more sensitive to changes of fixed values, such as thickness of material, its optical properties and/or uniformity.

Thus, the control site error indicator may include fitting merit function analyzer similar to that of FIG. 3, and/or structure parameter analyzer (metrology result analyzer) as exemplified in FIG. 6. In the latter case, the error indicator may utilize a thresholding technique with respect to the common parameter values, i.e. determine whether a difference between the common parameter values in the control site and actual measurement site exceeds a predetermined threshold.

Figure 7:
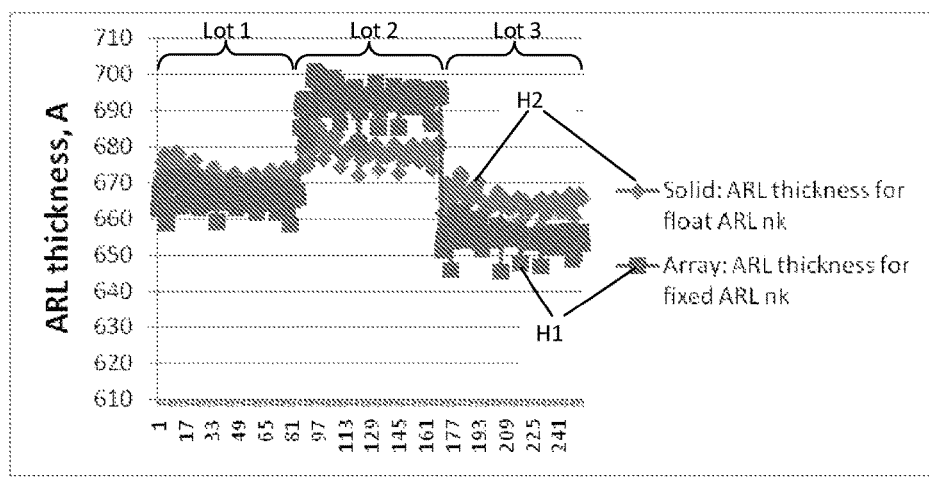
FIG. 7 illustrates thickness measurements of the layer in which material properties have changed as compared to the fixed properties, as measured on a non-patterned site (test site) in three different lots.

To this end, reference is made to FIG. 7 illustrating thickness measurements (structure parameter) of the layer in the control site in which material properties are floated (graph H2) as compared to measurement site with the fixed material properties (graph H1), as measured in three different lots Lot1, Lot2 and Lot3. The differences between the lots are much more pronounced for fixed n&k values. Alternatively or additionally, the error indicator may utilize identification of a sharp change in the values of different measurement parameters of control site(s). To minimize the TPT (throughput) hit, control site(s) sampling plan could be sparse, with one (or few) site per wafer, assuming that control site error indicators flag the problems that are not local in nature.

Figure 8:
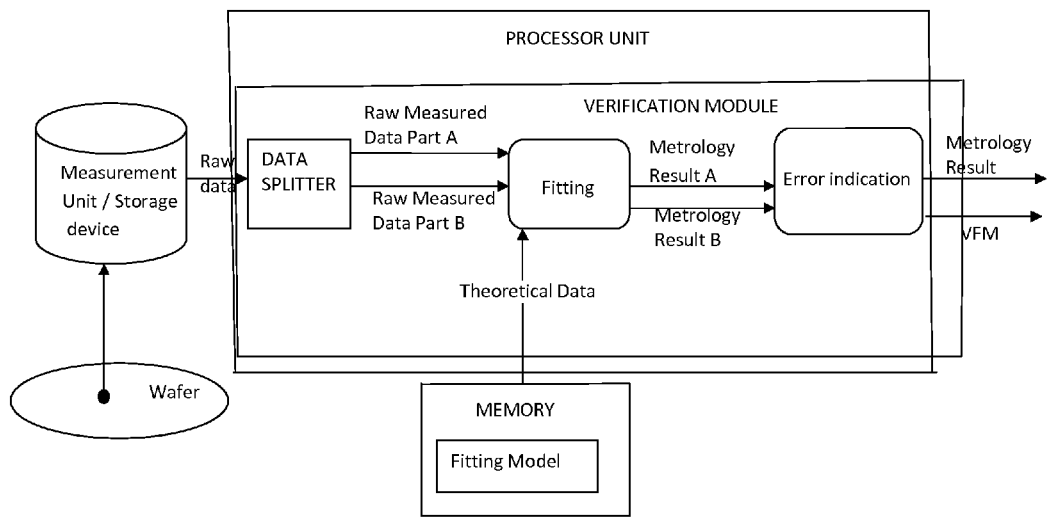
FIG. 8 exemplifies operation of the monitoring system of FIG. 1 in which the error indicator module includes a so-called differential measurement (data splitting) utility.

Reference is made to FIG. 8 exemplifying the operation of the monitoring system 100 in which the verification module 112 includes a so-called differential measurement (data splitting) utility. As shown in the figure, the processor unit includes a data splitter utility, which splits raw measured data (before fitting) into two raw data pieces/parts A and B (generally at least two data pieces) corresponding respectively to different measurement conditions. For example these may be different wavelengths of incident light, and/or different polarizations of incident light and/or different angle of incidence. More specifically, the raw measured data may be in the form of a spectral signature measured for a certain set of discrete wavelengths within a certain wavelength range, and the data splitter provides two spectral signature parts of said spectral signature for respectively odd and even wavelengths from said set of discrete wavelengths. The model fitting is applied to each of the raw data parts, and the same structure parameter (metrology result) is calculated for the measured data parts A and B. Then, the error indicator operates to compare between these parameter values and determined whether a difference exceeds a certain threshold.

The principles of this embodiment are associated with the following. One of questions that are frequently asked relates not to the mere existence of a possible bias, but to the possible size of the bias (error) to the parameter of interest due to the issue at hand. A possible way to achieve an estimation of this effect is by looking into the consistency of the interpretation by a method that could be termed "divide and compare". Usually, in all types of scatterometry tools, multiple data points are used together in order to establish the values of a few floating parameters, the number of data points much larger than the number of parameters (data points could be measurements taken at different wavelengths, incidence angles, polarizations or any combination). The common practice is to use all possible data points in order to produce a measurement that will have the best repeatability and accuracy. For the sake of verifying the accuracy and estimating the error of the interpretation the results may be compared to some reference. Such reference may be taken from the measured data itself by splitting the data into two parts and comparing the results. Preferably, the two data sets could have different characteristics, but similar repeatability. As indicated above, possible realization of the splitting could be: e.g. choosing different polarizations, splitting wavelength range at some point, using data from different angles, or some combination of the above. Having split the full data set as prescribed above it is possible now to run the interpretation three times—once with the full data set and once with each of the split sets. While the interpretation with the full set may be provided, a difference between the two partial sets can be used as an error indication for problems in the measurements.

It should be noted that in most cases, some difference between the results of the two data sets might occur even under normal condition. However, the level of these differences may increase, because the different parts respond differently to errors in the measurement or changes in the model assumptions, allowing setting threshold values that flag abnormal behavior. It should also be noted that actually the verification mode may be implemented by multiple such error indicators corresponding to the multiple floating parameters, allowing to select those parameters that are more indicative or allowing to track all of them, each with its own threshold level (that could be studied based on a preliminary data set during setup). Further, it should be noted that the error indications obtained in such verification are given in the units of the measured parameters (usually being nanometers or degrees). Although this unit similarity does not guarantee that the error indicators provide the real information of an error-bar of the measurement, under proper selection of the two sets of measured data the error indicators could be made roughly proportional up to a small factor to the real accuracy error, at least in magnitude. Also, if the interpretation time is not a limiting factor, several splits of the same data can be used in order to get additional error indicators, thus maximizing the sensitivity of the entire error indicator module.

Figure 9:
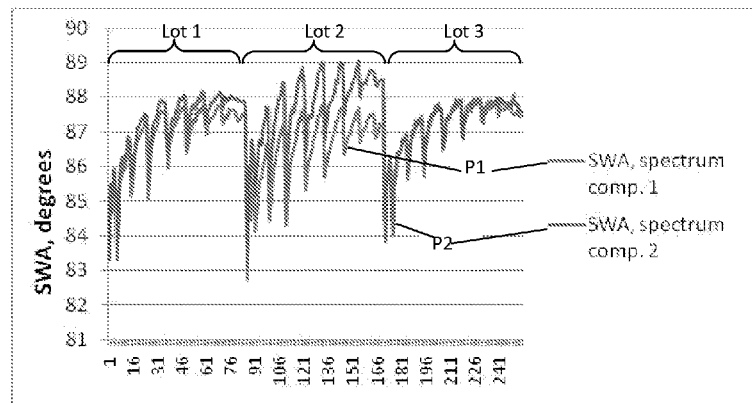
FIG. 9 illustrates graphically the principles of data splitting approach.

FIG. 9 illustrates graphically the principles of data splitting approach. In the figure, the measurement of the side wall angle (SWA) of the pattern is shown in the form of two splits of the measured data—graphs P1 and P2, which in this not limiting example correspond to different polarizations of incident light, for each of three lots Lot1, Lot2, and Lot3. As shown, the difference between the two data pieces is significant almost only for the measurements of Lot2. Thus, in this case, in both Lot1 and Lot3 it is clear seen that the two data sets (different polarizations in this case) agree well with one another, however in Lot2, in which material properties are incorrectly fixed, the differences between the values of the side wall angle measured separately by the two sets become significant, allowing to flag a problem using a threshold value.

Figure 10:
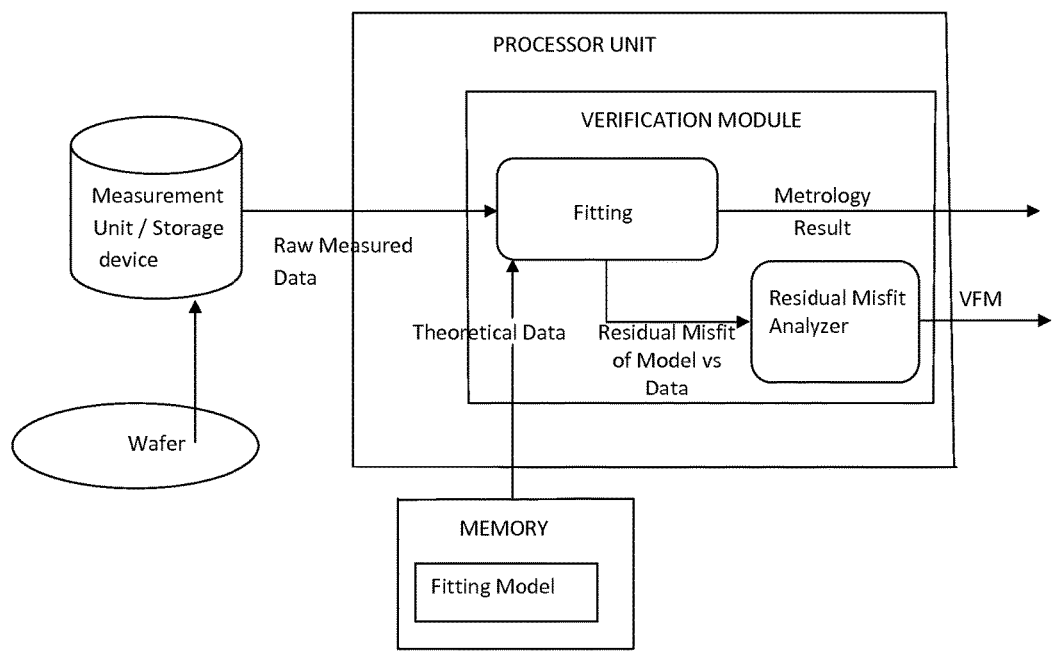
FIG. 10 exemplifies operation of the monitoring system of FIG. 1 in which the error indicator module includes a so-called residual misfit analyzer.

Referring to FIG. 10, there is exemplified the operation of the monitoring system 100 in which the verification module 112 includes a so-called residual misfit analyzer. According to this embodiment, a situation in which something has gone wrong is characterized by analyzing the spectral shape of the residual (e.g. residual error vs wavelength). In any realistic situation the fitting level at different parts of the signal, e.g. different spectral bands, is different, due to all sorts of measurement accuracy issues or modeling approximations or inaccuracies. Hence, typically the residual will have a clear, significant spectral shape beyond the random noise level. Accordingly, the spectral shape of the residual can be used as a fingerprint of the measurement, and by quantifying different parameters within this fingerprint situations in which some abnormal behavior has occurred, the abnormality can be identified. For example, a simple method may be to split the data into a few parts, e.g. different spectral bands, different polarizations, etc. as described above, and calculate the mean square error between the best fit and the measurement for each part separately. By following over the errors in specific parts (e.g. error in the UV part of the spectrum), or functions of them (e.g. the ratio between the error in the UV to the error in the IR), it is possible to obtain meaningful error indicators that can be studied during setup and compared to a threshold for flagging abnormal behavior. Also, a more technically complex attitudes, such as using different transforms, moments or classification techniques for identifying a change in the residual signal vs. the typical fingerprint learned during the setup, can also be employed.

Figure 11:
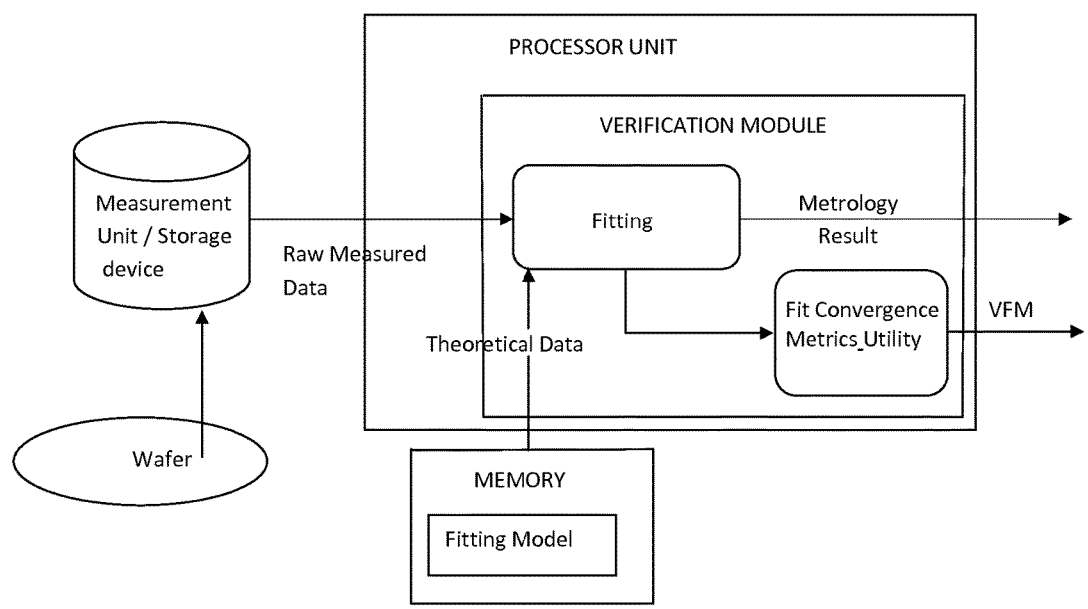
FIG. 11 exemplifies an embodiment of the invention where the error indicator module includes a fit convergence metrics utility.

Reference is now made to FIG. 11 exemplifying yet further embodiment of the invention where the verification module 112 includes a fit convergence metrics_utility. This indicator utility determines a possible mismatch between the model and the measured data at the dynamics of the convergence algorithm. The inventors have found that when an error exists in the measured data or in the model, the convergence from the initial point to the best fit takes longer than usually, i.e. the number of iterations required is larger. Hence it is possible to flag a potential problem whenever convergence is larger than a statistically validated number of iterations defined during recipe setup. More specifically, the processor utility operates to apply the selected fitting model to the raw measured data (measured radiation response of one or more measurement sites to incident radiation, where this fitting procedure includes one or more iteration steps until a best fit condition is achieved. The verification mode includes analyzing a number of the iteration steps applied to arrive to the best fit condition, to determine whether this number exceeds a certain threshold, to thereby identify the unacceptable condition for the measured data.

Figure 12:
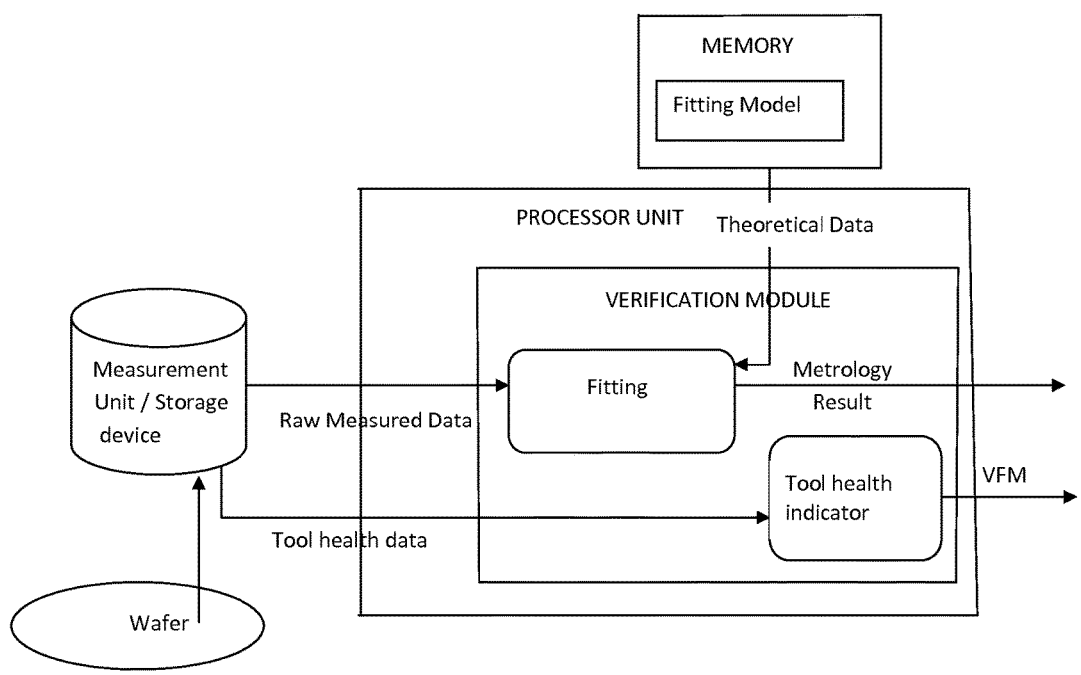
FIG. 12 exemplifies an embodiment of the invention where the error indicator module utilizes the verification mode based on analysis of the tool health data.

Reference is now made to FIG. 12 showing yet further embodiment of the invention where the verification mode utilizes analysis of the measurement health data. Measurement health indicators preferably could cover both hardware (HW) performance quality and possible mismatch between the sample and measurement recipe. Any measurement health indicators can indicate a possible impact on metrology reliability. Inputs include parameters that characterize measurement system during the measurements, such as illumination intensity and stability, pattern recognition quality, location deviation of the measurement from the target (e.g. due to possible mismatch between the sample and measurement recipe), focus quality of the measurements, etc. In that case when the quality score deteriorates below some pre-defined value, it could be used as an indication of error.

It should also be noted, that the error indicator module may be configured and operable to determine the measured parameters confidence and score limits During setup of recipe, the set of samples representing real process variations is being studied. Based on the results statistically confidence limits are set for all measured parameters to be later used for calculation of the score of the measurement of production samples. Score limits are also set to indicate boundaries of the recipe or the possible range of parameters where recipe is valid.

It should be noted that all or some of the above exemplified error indicator utilities can be used as single site indicators and as wafer statistical indicators (wafer average, range, standard deviation, etc). There may be additional indicators that can be used on the wafer level only.

Figure 13:
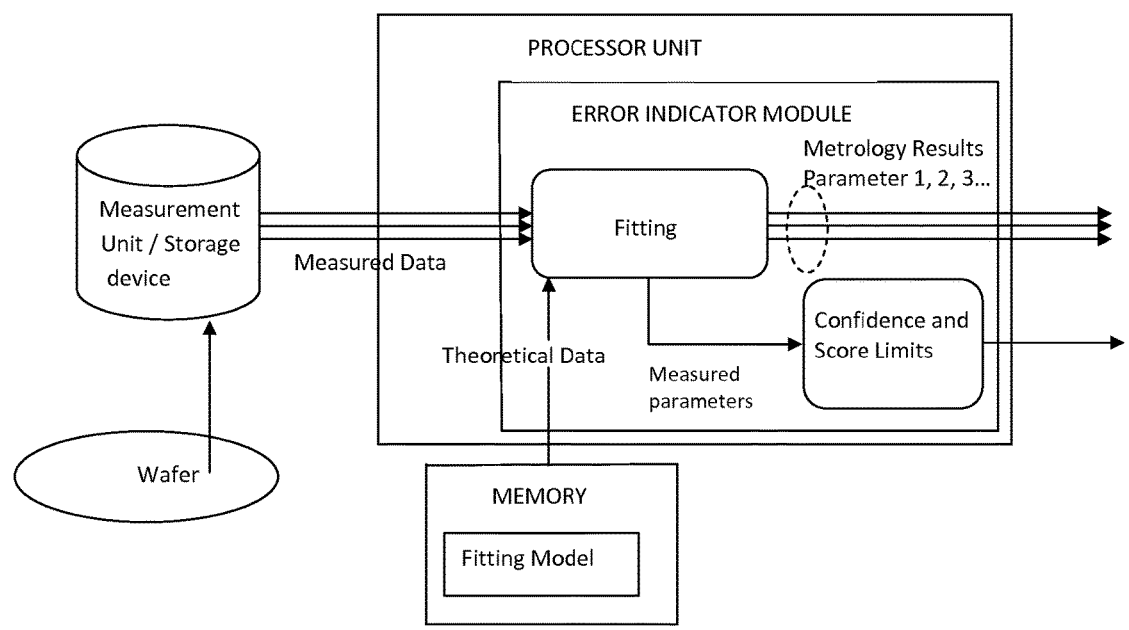
FIG. 13 exemplifies an embodiment of the invention where the error indicator module determines the measured parameters confidence and score limits by monitoring the across wafer fingerprint.

Referring to FIG. 13, there is exemplified the verification module configured and operable for determining the measured parameters confidence and score limits by monitoring the across wafer fingerprint. Measured parameters often have a typical process related across-wafer spatial fingerprint, e.g. constant, center-to-edge, etc. Changes in the spatial fingerprint may be used as indication of a problem. For example, a fixed parameter that has a spatial fingerprint is changing and creates a non-constant spatial fingerprint in a parameter that is usually uniform, as indicated by the across-wafer variation. Also, a disturbance of the circular symmetry spatial fingerprint which is typical to many process steps, can be identified by the breaking of rotational symmetry. By knowing across the wafer variations from the setup stage, it is possible to determine whether there is a single outlier (flier) measurement, when one of the measurement points are far away from the wafer median value, or from the expected distribution or if all measurements on the wafer are not reliable. Thus, the measured data may be provided in the form a multi-point function of a measured response of the structure to incident radiation, and the verification mode includes comparing the multi-point function of a measured response with a theoretical model-based function corresponding to a predetermined degree of fit with the measured response, to determine whether the multi-point function includes at least one function value for at least one measurement point that differs from the function values at other measurement points by a value exceeding certain threshold.

As indicated above, in order to provide a unified monitoring system all or at least some of the above exemplified error indicator utilities could be combined into a single verification figure of merit (VFM) available to the user. VMF can be calculated for each measurement sample (site or die), and for the wafer. The die (measurement site or die) VFM may combine all or some error indicators related to the specific measurement site or die. The wafer VFM may combine together all dies' VFMs and add wafer related statistical and fingerprint error indicators related to the wafer.

Fuzzy logic approach could be used to combine all the error indicators together first on the site or die level, and then on the wafer level. This may be a rule-based combination, according to which each error indicator is assigned a threshold (or two thresholds, minimum and maximum, as the case may be). Optionally, for each indicator a warning zone is also defined around the threshold. Each error indicator is then assessed an assigned one of three discrete states: Pass ("green light"), fail ("red light") or warning ("yellow light"). Having the states of all individual error indicators, rules may be defined in the spirit of the well known Western Electric Rules, such as, for example, if at least three indicators are in the red zone then the total result is "Fail", if at least one indicator is "Fail" and at least two indicators are "Warning" then the total result is "Warning", etc.

In the spirit of Fuzzy logic it is possible to define a value between 0 and 1 for each error indicator where values in the Fail region get 0, in the Pass region get 1 and in-between the values are monotonously (e.g. linearly) interpolated. The total value can be obtained for example by first combining all the values for the different error indicators and then comparing the result to a threshold (to define warning message). Combining the error indicators could be done based on user define weights per each indicator, to allow user define the most important or most relevant indicators. This type of logic could also be implemented in a multi-level fashion. For example, the error indicators are grouped together and the fuzzy logic value for all members of each group is summed up; for each group a threshold level is defined and a fuzzy-logic value is assigned based on the relation between the sum of the group and the threshold; the group results are added and compared to threshold in order to get the final value. The potential advantage of such a system over a discrete rule base method could be in complex situations and in cases in which seemingly contradicting information has to be evaluated.

Also, the technique based on a learning system can be used that maps the phase-space of normal error indicator values and learns how to differentiate between normal behavior and abnormal one. Normal behavior examples are taken from a qualified data set achieved using a healthy tool and a qualified measurement process. In order to provide a training set for abnormal behavior the model fixed parameters could be deliberately shifted or the measured values could be deliberately skewed in modes similar to known hardware issues, e.g. addition of random gain or random noise. Once provided with the two data sets, the learning system (e.g. an artificial neural network) can be trained to separate between good and bad measurements. The system is then used during the run time to classify each new measurement.

The invention claimed is:

1. A process control method for manufacturing semiconductors devices using measurements of parameters of patterned structures, said measurements of the parameters of patterned structures being based on a predetermined fitting model, the method comprising:

(a) applying one or more optical measurements to at least one patterned structure of a semiconductor wafer and generating measured data indicative of the one or more optical measurements in the at least one patterned structure, the one or more optical measurements being measurement of one or more parameters of the patterned structure including at least one of: layer thickness, optical critical dimensions, width of features of the patterned structure, height profile of features of the patterned structure, spacing between features of the pattern structure, and optical properties of materials of the patterned structure, the one or more optical measurements including
applying incident radiation to the structure and
detecting one or more optical response signals of the structure to the incident radiation, the measured data indicative of the one or more optical measurements including raw data which comprises at least one signature corresponding to an optical response of the structure to the incident radiation;

(b) providing additional data including at least one of: measurement health data, data corresponding to a desired degree of fit with the predetermined fitting model, and one or more structure parameters determined from a fitting procedure; and (c) upon receiving the measured data by a computer system having a data input utility, a non-transitory computer readable memory, and a data processor, processing the measured data by the data processor, the processing including verifying the measured data to identify whether the measured data provides for obtaining therefrom an acceptable measurement result for one or more parameters of the patterned structure, the verifying of the measured data including
applying to the raw data and the additional data a combination of two or more different verification modes based on analysis of the raw data and the additional data, each verification mode being configured to, upon determining one or more measurement problems of a different type, generate one or more corresponding error indicators indicative of a potentially erroneous measurement, combining the error indicators of the two or more verification modes based on user defined weights assigned to the error indicators, and applying threshold based analysis to the error indicators using a predetermined control limit to classify the raw data as corresponding to acceptable or unacceptable measurement providing, respectively, acceptable or unacceptable measurement result, and, upon classifying the raw data as corresponding to the acceptable or unacceptable measurement, applying further processing by a fitting procedure using a predetermined fitting model to the raw data corresponding to the acceptable measurement result to determine the measurement result for one or more parameters of the patterned structure, and determining whether the raw data corresponding to the unacceptable measurement are to be disregarded from further processing by the fitting procedure to determine the measurement result for one or more parameters of the patterned structure, or whether one or more parameters of the fitting model are to be modified.

2. The method of claim 1, further comprising providing data indicative of a desired degree of fit with the fitting model, the desired degree of fit being defined by a merit function or goodness of fit factor.

3. The method of claim 2, wherein the applying of the selected verification mode comprises analyzing multiple values of the merit function determined for multiple measurement sites respectively, and upon determining that the multiple values of the merit function include at least one value that differs from other of the multiple values by a value exceeding a certain threshold defined by a control limit of the verification mode, classifying the corresponding measurement as potentially erroneous measurement.

4. The method of claim 3, wherein the multiple measurement sites comprise at least one control site having a configuration corresponding to at least one other measurement site and being characterized by a smaller number of floating parameters of the patterned structure as compared to the at least one other measurement site.

5. The method of claim 3, wherein the applying of the selected verification mode comprises analyzing at least two merit functions determined for a control site and at least one other measurement site respectively, and upon determining that a difference between the merit functions of the control site and the at least one other measurement site differs by a value exceeding a certain threshold defined by a control limit of the verification mode, classifying the corresponding measurement as the potentially erroneous measurement.

6. The method of claim 3, further comprising utilizing the merit function and determining a measurement result in the form of at least one parameter of the patterned structure, for each of a control site and at least one other measurement site, wherein the control site has a configuration corresponding to the at least one other measurement site and being characterized by a smaller number of floating parameters of the patterned structure as compared to that of the other measurement site.

7. The method of claim 1, wherein the verification modes based on analysis of the raw data and the additional data comprises at least one of the following:

determining whether a change in spatial fingerprint of the raw data across the structure being measured is above a threshold;

determining whether an average of the raw data is above a threshold.

8. The method of claim 2, wherein the measured data comprises at least two measured data pieces corresponding to at least two measurements obtained with different measurement conditions, respectively, the analyzing of the measured data comprising, for each of the at least two measured data pieces, utilizing at least one model based measured parameter corresponding to a predetermined degree of fit with the raw data piece and determining the at least one parameter of the patterned structure;

the applying of the selected verification mode comprising analyzing at least two values of the at least one parameter of the patterned structure corresponding to the at least two different measurement conditions, and upon determining that a difference between the at least two values exceeds a certain threshold defined by a control limit of the verification mode, classifying the corresponding measurement as the potentially erroneous measurement.

9. The method of claim 8, wherein the data indicative of measurements comprise spectral data, the at least two measured data pieces corresponding to at least two different sets of wavelengths respectively.

10. The method of claim 8, wherein the at least two measured data pieces correspond to at least two different angles of incidence of radiation onto the patterned structure, and/or angles of radiation propagation from the structure, utilized in the measurements.

11. The method of claim 8, wherein the at least two measured data pieces correspond to at least two different polarizations of radiation utilized in the measurements.

12. The method of claim 1, wherein the raw data is in the form of a multi-point function of a detected response of the patterned structure to incident radiation corresponding to multiple measurements at multiple measurement sites of the structure, the applying of the selected verification mode further comprises comparing the multi-point function of a measured response with a theoretical model-based function corresponding to a predetermined degree of fit with the measured response, and upon determining that the multi-point function includes at least one function value for at least one measurement point that differs from the function values at other measurement points by a value exceeding a certain threshold being a predefined control limit of the verification mode, classifying the measured data as the potentially erroneous measurement.

13. The method of claim 2, wherein the applying of the selected verification mode further comprises determining a number of iteration steps applied to reach the desired goodness of fit condition, and upon identifying that the number exceeds a certain threshold defined by a control limit of the verification mode, classifying the corresponding measurement as the potentially erroneous measurement.

14. The method of claim 1, wherein the raw data corresponds to the measurements performed on the same measurement site and comprising measured signals successively obtained from the measurement site.

15. The method of claim 14, wherein the raw data further comprises an integrated measured signal formed by a series of measured signals successively measured 011 the same measurement site.

16. The method of claim 14, wherein the selected verification mode comprises comparing the measured signals of the series of measured signals with one another, and upon determining that the measured signals include at least one measured signal that differs from other measured signals by a value exceeding a certain threshold defined by a control limit of the verification mode, classifying the corresponding measurement as the potentially erroneous measurement.

17. The method of claim 15, wherein the selected verification mode comprises comparing the measured signals of the series of measured signals with the integrated measured signal, and upon determining that the measured signals include at least one measured signal that differs from the integrated measured signal by a value exceeding a certain threshold defined by a control limit of the verification mode, classifying the corresponding measurement as the potentially erroneous measurement.

18. A system for process control of manufacturing semiconductors devices, the system controlling measurements of parameters of patterned structures, the system comprising:
  (a) an optical measurement unit configured and operable to apply one or more optical measurements to a patterned structure of a semiconductor wafer and generate measured data indicative of the one or more optical measurements in the at least one patterned structure,
    the one or more optical measurements being measurement of one or more parameters of the patterned structure including at least one of layer thickness, optical critical dimensions, width of features of the patterned structure, height profile of features of the patterned structure, spacing between features of the pattern structure, and optical properties of materials of the patterned structure,
    the one or more optical measurements including applying incident radiation to the structure and detecting one or more optical response signals of the structure to the incident radiation, the measured data indicative of the one or more optical measurements including raw data comprising at least one signature corresponding to an optical response of the structure to the incident radiation; and
  (b) a data verification system comprising a computer system configured for data communication with the optical measurement unit and comprising a data input utility configured to receive the raw data;
  a non-transitory computer readable memory utility storing at least one fitting model; and
  a data processor utility, the data processor utility comprising:
  a fitting utility configured and operable to apply a fitting procedure to the measured data using the at least one fitting model;
  a verification module comprising:
    two or more error indicator utilities configured and operable to apply to the raw data and to additional data two or more different verification modes selected based on analysis of the raw data and the additional data, the additional data including at least one of: measurement health data, data corresponding to a desired degree of fit with the predetermined fitting model, and a one or more structure parameters calculated from a fitting procedure, such that each error indicator utility is operable to apply one or two of the two or more verification modes, and, upon determining one or more measurement problems of a different type, generate one or more corresponding error indicators indicative of a potentially erroneous measurement; and
    a Verification Figure of Merit utility configured and operable to
      combine the error indicators of the two or more error indicator utilities based on user defined weights assigned to the error indicators, and
      apply threshold based analysis to the error indicators using a predetermined control limit to classify the raw data as corresponding to acceptable or unacceptable measurement providing, respectively, acceptable or unacceptable measurement result, and, upon classifying the raw data as corresponding to acceptable measurement,
      apply a fitting procedure with a predetermined fitting model to the raw data corresponding to the acceptable measurement result to determine a measurement result for one or more parameters of the patterned structure, and
      determine
        whether the raw data corresponding to the unacceptable measurement are to be disregarded from further processing by the fitting procedure to determine the measurement result for one or more parameters of the patterned structure, or
        whether one or more parameters of the fitting model are to be modified.

19. The method of claim 1, wherein said signature corresponding to the optical response of the structure to the incident radiation comprises at least one of spectral and diffractive signature.

20. The method of claim 1, wherein said applying of the two or more different verification modes further comprises analysis of predetermined confidence and score limits defined by one or more measurement recipes for two or more verification modes.

21. The system of claim 18, wherein the two or more error indicator utilities are configured and operable to apply to the raw data two or more different verification modes selected based on analysis of predetermined confidence and score limits defined by one or more measurement recipes for two or more verification mode.

* * * * *